(12) United States Patent
Wilkinson et al.

(10) Patent No.: US 6,936,036 B2
(45) Date of Patent: Aug. 30, 2005

(54) BLOOD COLLECTION AGENCY

(75) Inventors: Bradley M. Wilkinson, North Haledon, NJ (US); Kirk D. Swenson, North Caldwell, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/219,372

(22) Filed: Aug. 15, 2002

(65) Prior Publication Data

US 2003/0036731 A1 Feb. 20, 2003

Related U.S. Application Data

(60) Provisional application No. 60/313,047, filed on Aug. 17, 2001.

(51) Int. Cl.$^7$ .............................. A61M 5/00; A61M 5/32
(52) U.S. Cl. ........................................ 604/263; 604/198
(58) Field of Search ........................ 604/164.08, 164.07, 604/165.03, 263, 168.01, 177, 192, 198, 110; 128/919; 600/576

(56) References Cited

U.S. PATENT DOCUMENTS

| | | | | |
|---|---|---|---|---|
| 4,867,172 A | * | 9/1989 | Haber et al. | |
| 4,929,241 A | * | 5/1990 | Kulli | |
| 4,935,013 A | * | 6/1990 | Haber et al. | |
| 5,120,320 A | * | 6/1992 | Fayngold | |
| 5,192,275 A | * | 3/1993 | Burns | |
| 5,348,544 A | * | 9/1994 | Sweeney et al. | |
| 5,425,720 A | * | 6/1995 | Rogalsky et al. | |
| 5,538,508 A | * | 7/1996 | Steyn | |
| 5,700,249 A | * | 12/1997 | Jenkins | 604/263 |
| 5,713,872 A | * | 2/1998 | Feuerborn et al. | |
| 5,735,827 A | * | 4/1998 | Adwers et al. | |
| 5,743,888 A | * | 4/1998 | Wilkes et al. | |
| 5,779,684 A | * | 7/1998 | Tamaro | |
| 5,910,130 A | * | 6/1999 | Caizza et al. | 604/198 |
| 5,925,020 A | * | 7/1999 | Nestell | |
| 5,951,525 A | * | 9/1999 | Thorne et al. | 604/198 |

(Continued)

FOREIGN PATENT DOCUMENTS

| | | | |
|---|---|---|---|
| EP | 0713710 A1 | * | 5/1996 |
| EP | 1132103 A1 | * | 9/2001 |
| FR | 2789317 | * | 2/1999 |
| FR | 2789317 A1 | * | 8/2000 |

*Primary Examiner*—Nicholas D. Lucchesi
*Assistant Examiner*—Matthew F DeSanto

(57) ABSTRACT

The present invention is directed to a low cost shieldable safety needle assembly. The assembly includes a needle cannula and a tip guard axially movable along the needle cannula through a drive mechanism. The drive mechanism may be interconnected between the tip guard and the needle cannula through a hub. The tip guard is axially movable along the needle cannula from a proximal position substantially adjacent a proximal end of the needle cannula at the hub, to a distal position in which the tip guard protectively surrounds the distal end of the needle cannula, thus effectively shielding the puncture tip of the needle. The drive mechanism is a unitary structure which is capable of maintaining a first self-supporting shape for maintaining the tip guard in the proximal position and is deflectable from the first self-supporting shape to a second extended shape in which the tip guard is moved to the distal position. The drive mechanism may be a rigid flexible planar sheet material which includes a plurality of folds for defining the self-supporting shape. The needle assembly may include structure for mating with a hypodermic syringe, a blood collection set, or other medical device.

26 Claims, 13 Drawing Sheets

U.S. PATENT DOCUMENTS

| | | |
|---|---|---|
| 5,957,892 A | 9/1999 | Thorne |
| 6,015,397 A | 1/2000 | Elson et al. |
| 6,234,999 B1 * | 5/2001 | Wemmert et al. |
| 6,254,577 B1 * | 7/2001 | Huet |
| 6,280,420 B1 * | 8/2001 | Ferguson et al. |
| 6,537,259 B1 * | 3/2003 | Niermann .................. 604/263 |
| 2001/0039401 A1 | 11/2001 | Ferguson et al. |
| 2002/0065488 A1 * | 5/2002 | Suzuki et al. |

* cited by examiner

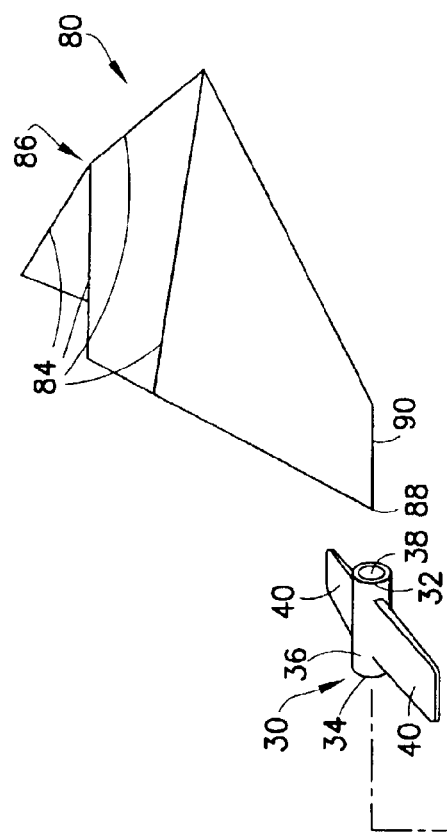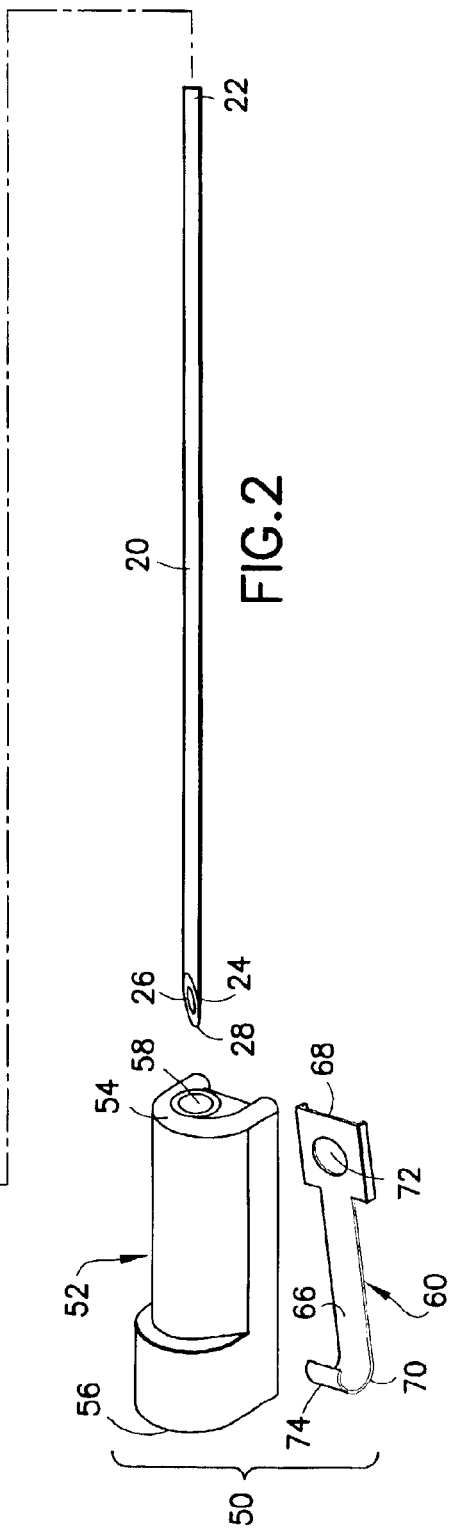
FIG.2

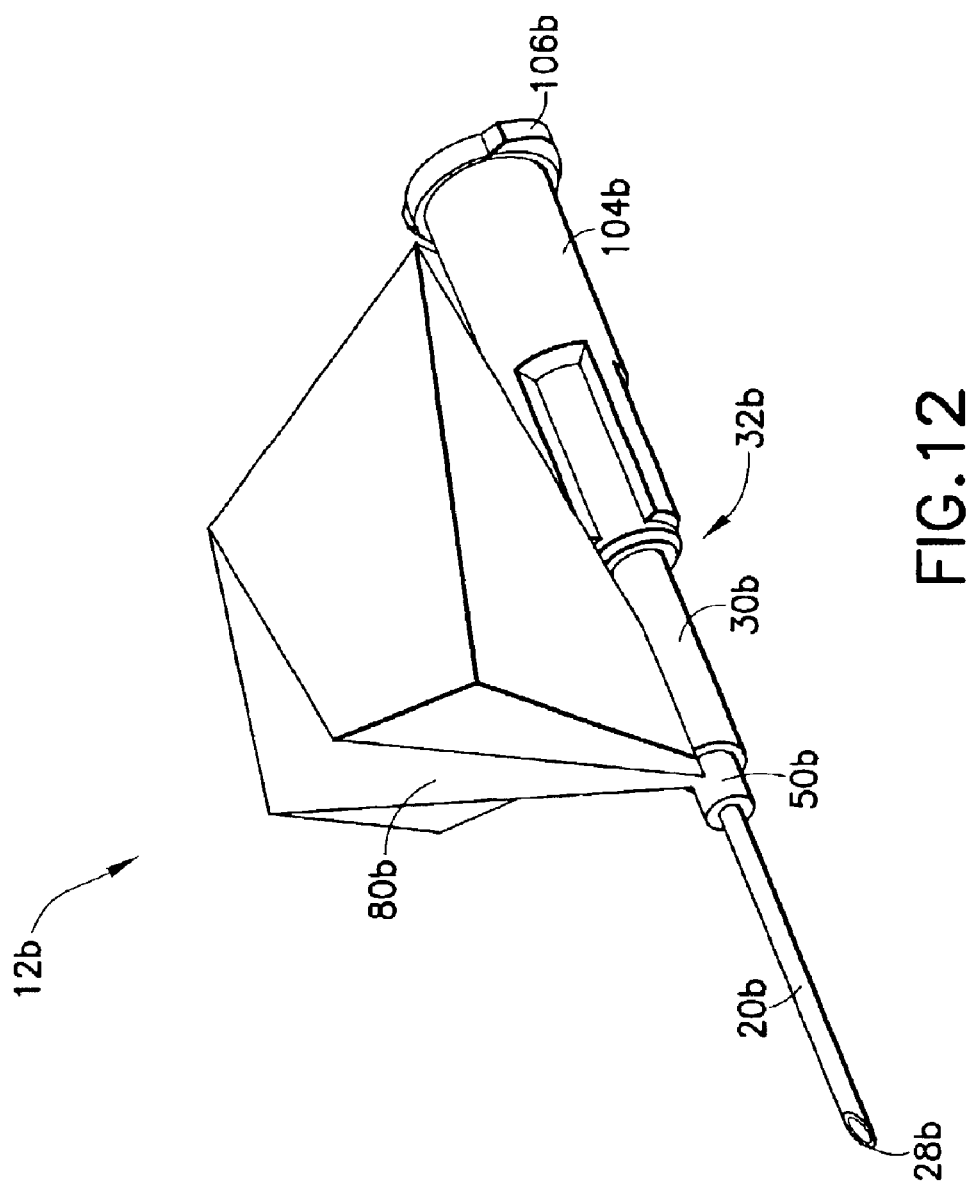

BLOOD COLLECTION AGENCY

This application claims priority to U.S. Provisional Application Ser. No. 60/313,047 filed Aug. 17, 2001, entitled "Blood Collection Set".

BACKGROUND OF THE INVENTION

1. Field of the Invention

The present invention relates to safety needle assemblies for safe and convenient handling of needles. More particularly, the present invention relates to a low cost needle assembly having a safety shield.

2. Description of Related Art

Disposable medical devices having piercing elements are typically used for administering a medication or withdrawing a fluid, such as hypodermic syringes, blood collecting needles, fluid handling needles and assemblies thereof. Current medical practice requires that the fluid containers and needle assemblies used in such systems be inexpensive and readily disposable. Safe and convenient handling of disposable medical devices results in the disposal of the medical devices intact.

For example, existing blood collection systems typically employ some form of durable, reusable holder on which detachable and disposable needles and fluid collection tubes may be mounted. A blood collection system of this nature can be assembled prior to use and then disassembled after usage. Thus, these blood collection systems allow repeated use of the relatively expensive holder upon replacement of the relatively inexpensive needle and/or fluid collection tube. In addition to reducing the cost of collecting blood specimens, these blood collection systems also help minimize the production of hazardous medical waste. A blood collection set or intravenous (IV) infusion set typically includes a needle cannula having a proximal end, a pointed distal end and a lumen extending therebetween. The proximal end of the needle cannula is securely mounted in a plastic hub with a central passage that communicates with the lumen through the needle cannula. A thin flexible thermoplastic tube is connected to the hub and communicates with the lumen of the needle cannula. The end of the plastic tube remote from the needle cannula may include a fixture for connecting the needle cannula to a blood collection tube or some other receptacle. The specific construction of the fixture will depend upon the characteristics of the receptacle to which the fixture will be connected.

In order to reduce the risk of incurring an accidental needle-stick wound, protection of used needle tips becomes important. With concern about infection and transmission of diseases, methods and devices to enclose the used disposable needle have become very important and in great demand. For example, needle assemblies commonly employ a safety shield that can be moved into shielding engagement with a used needle cannula without risking an accidental needle stick.

Some needle shields are referred to as tip guards, and include a small rigid guard that can be telescoped along the length of a needle cannula and extended over the puncture tip of the needle for protection. Such conventional tip guard may include some form of tether for limiting the travel of the tip guard to the length of the needle cannula. Additionally, such conventional tip guard typically includes structure that lockingly engages over the tip of the used needle cannula to prevent a re-exposure of the needle. The structure for preventing re-exposure may include a metallic spring clip or a transverse wall integrally formed with one end of the tip guard. Needle assemblies including such tip guards, however, typically include extensive mechanics for positioning of the tip guard, resulting in complex arrangements which are costly to manufacture and assembly. Also, operation of the tip guard can involve substantial manipulation by the user to extend the tip guard to a shielding position.

Accordingly, a need exists for a needle assembly for use with disposable medical devices, such as a blood collection set, which achieves secure and effective shielding of a used needle tip and which is simple and inexpensive to manufacture and easy to operate.

SUMMARY OF THE INVENTION

The present invention is directed to a shieldable needle device, particularly useful in connection with a blood collection set. The needle device includes a needle cannula having opposed proximal and distal ends and a tip guard axially movable along the needle cannula from a proximal position substantially adjacent the proximal end of the needle cannula to a distal position where the tip guard protectively surrounds the distal end of the needle cannula. A drive mechanism is connected to the tip guard for moving the tip guard from the proximal position to the distal position. The drive mechanism is a unitary structure capable of maintaining a first self-supporting shape for maintaining the tip guard in the proximal position, and is deflectable from the first self-supporting shape to a second extended shape in which the tip guard is moved to the distal position. Desirably, the drive mechanism is a unitary structure of a rigid flexible planar sheet material, such as paper or plastic, which including a plurality of folds.

The needle device may include a hub mounted to the proximal end of the needle cannula, with the drive mechanism interconnecting the hub and the tip guard. Desirably, the drive mechanism is in the form of a dorsal fin extending along the needle device.

The present invention is also directed to a shieldable needle device which includes a needle cannula having opposed proximal and distal ends, a hub mounted to the proximal end of the needle cannula, and a tip guard axially movable along the needle cannula from a proximal position substantially adjacent the hub to a distal position, in which the tip guard protectively surrounds the distal end of the needle cannula, such as a puncture tip. The needle device further includes a drive mechanism for moving the tip guard from the proximal position to the distal position. The drive mechanism includes a planar material interconnected between the hub and the tip guard, desirably a rigid flexible material such as a sheet of paper or polypropylene plastic, folded into the form of a dorsal fin extending along the needle device. The planar material has a plurality of folds for providing the drive mechanism with at least one trigger and at least one hinge. The trigger and the hinges interrelate to deflect the drive mechanism for movement of the tip guard from the proximal position to the distal position upon activation of the trigger. For example, external pressure exerted on the trigger causes at least one of the plurality of folds to unfold and act as a hinge, thereby activating the drive mechanism and causing the tip guard to move to the distal position.

The tip guard may include a tip guard housing formed from a plastic material and a metallic spring clip mounted to the housing. The spring clip may be biased against the needle cannula when the tip guard is in the proximal position, and may be resiliently moved over the distal end of the needle cannula when the tip guard is in the distal position. Moreover, the hub may be adapted for connection to a flexible tube of a blood collection set.

In a further embodiment, the present invention is directed to a shieldable blood collection set which includes a fixture for connecting the blood collection set to a receptacle; a flexible tube having opposed first and second ends, with the first end of the flexible tube being connected to the fixture; a hub mounted to the second end of the flexible tube; a needle cannula having a proximal end connected to the hub, a distal end projecting from the hub and a lumen in fluid communication with the tube and the fixture; a tip guard axially movable along the needle cannula from a proximal position substantially adjacent the hub to a distal position surrounding the distal end of the needle cannula; and a drive mechanism for moving the tip guard from the proximal position to the distal position. The drive mechanism includes a planar material securely interconnected between the hub and the tip guard, with the planar material including a plurality of folds forming at least one trigger for activation of the drive mechanism and at least one hinge capable of moving the tip guard from the proximal position to the distal position. External pressure exerted on the trigger causes at least one of the plurality of folds to unfold and act as a hinge, thereby activating the drive mechanism and causing the tip guard to move to the distal position.

DESCRIPTION OF THE DRAWINGS

FIG. 2 is an exploded perspective view of the shieldable needle assembly of the blood collection set of FIG. 1;

FIG. 11 is cross-sectional view of the shieldable needle assembly of FIG. 10 in an extended shielded position including the alternate tip guard of FIG. 9;

FIG. 12 is a perspective view of a needle assembly for attachment to a syringe in accordance with a further embodiment of the present invention;

DETAILED DESCRIPTION

Figure 1:
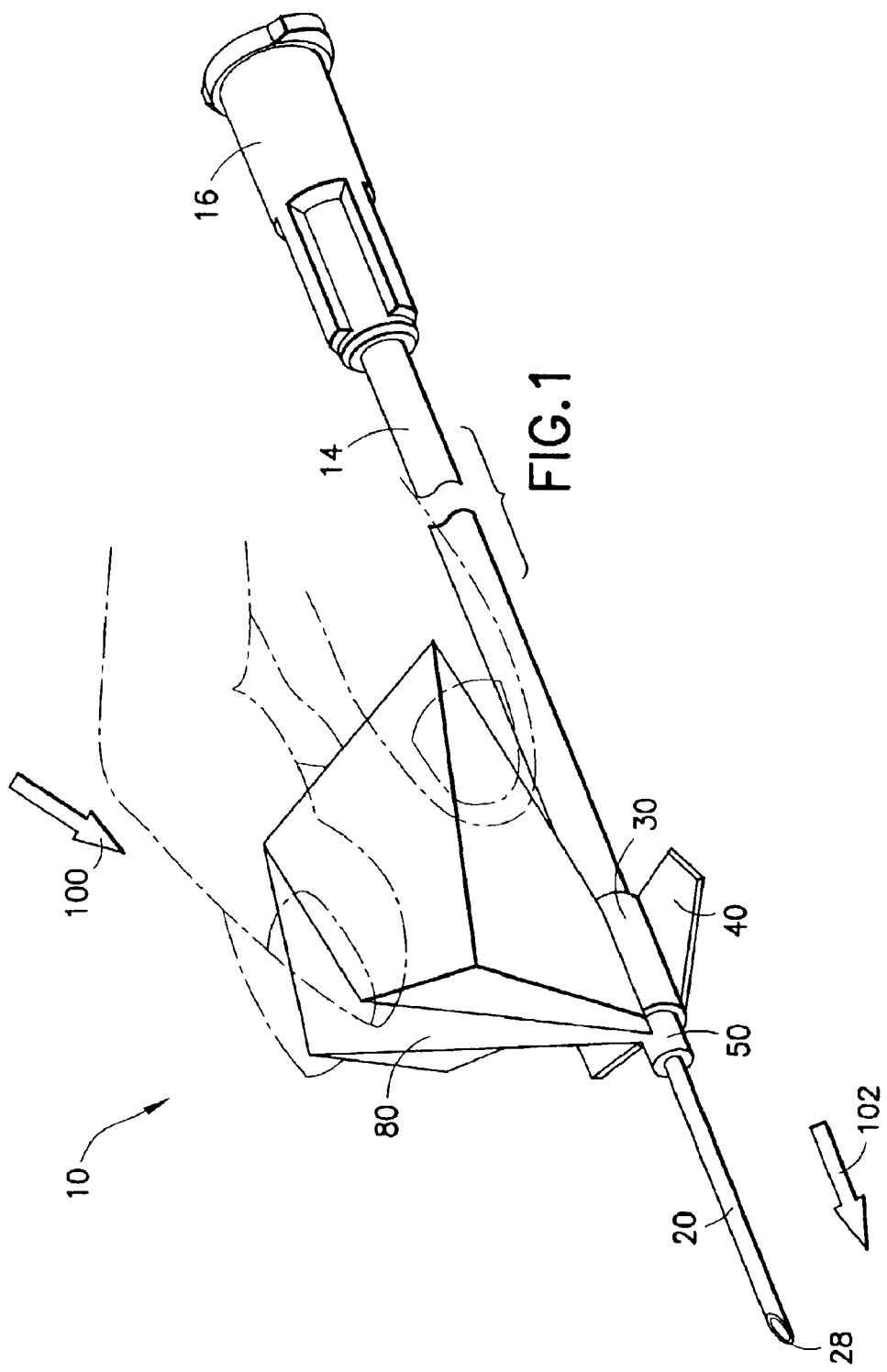
FIG. 1 is a perspective view of a blood collection set in accordance with the present invention.
Figure 3:
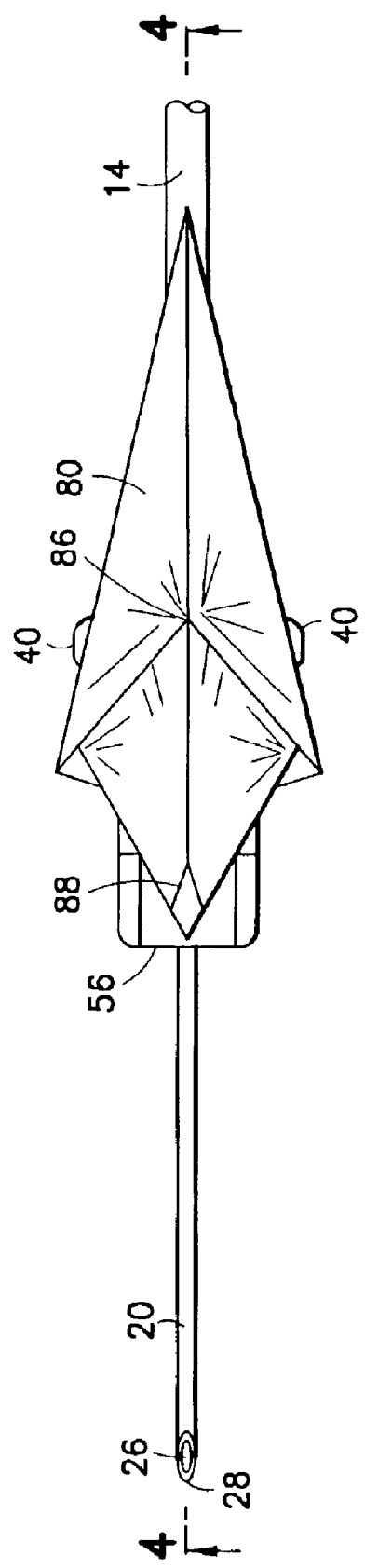
FIG. 3 is a top plan view of the shieldable needle assembly in a retracted position.
Figure 4:
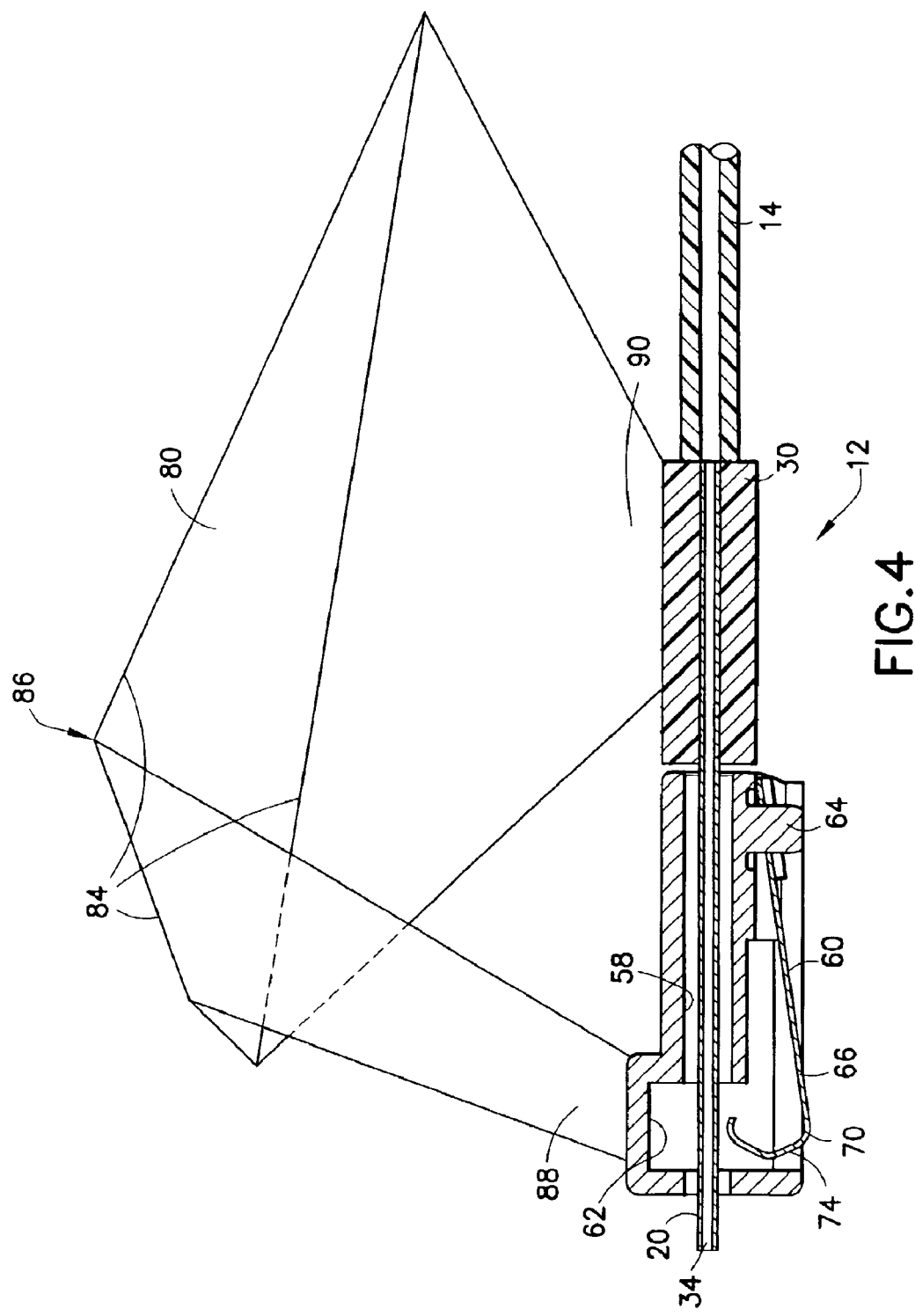
FIG. 4 is a cross-sectional view taken along line 4—4 of FIG. 3.
Figure 5:
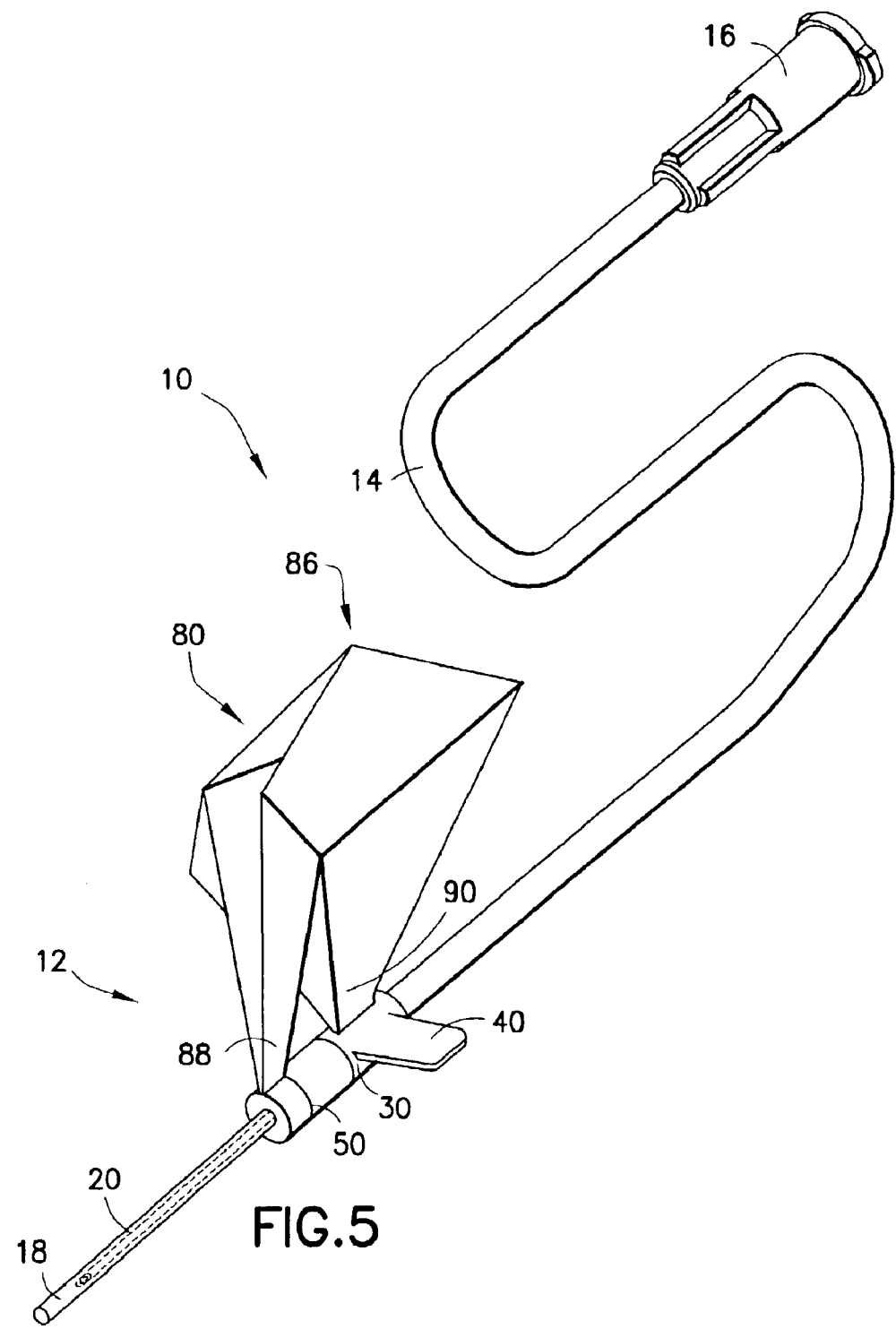
FIG. 5 is a perspective view of the fully assembled blood collection set with a packaging cover thereon.
Figure 6:
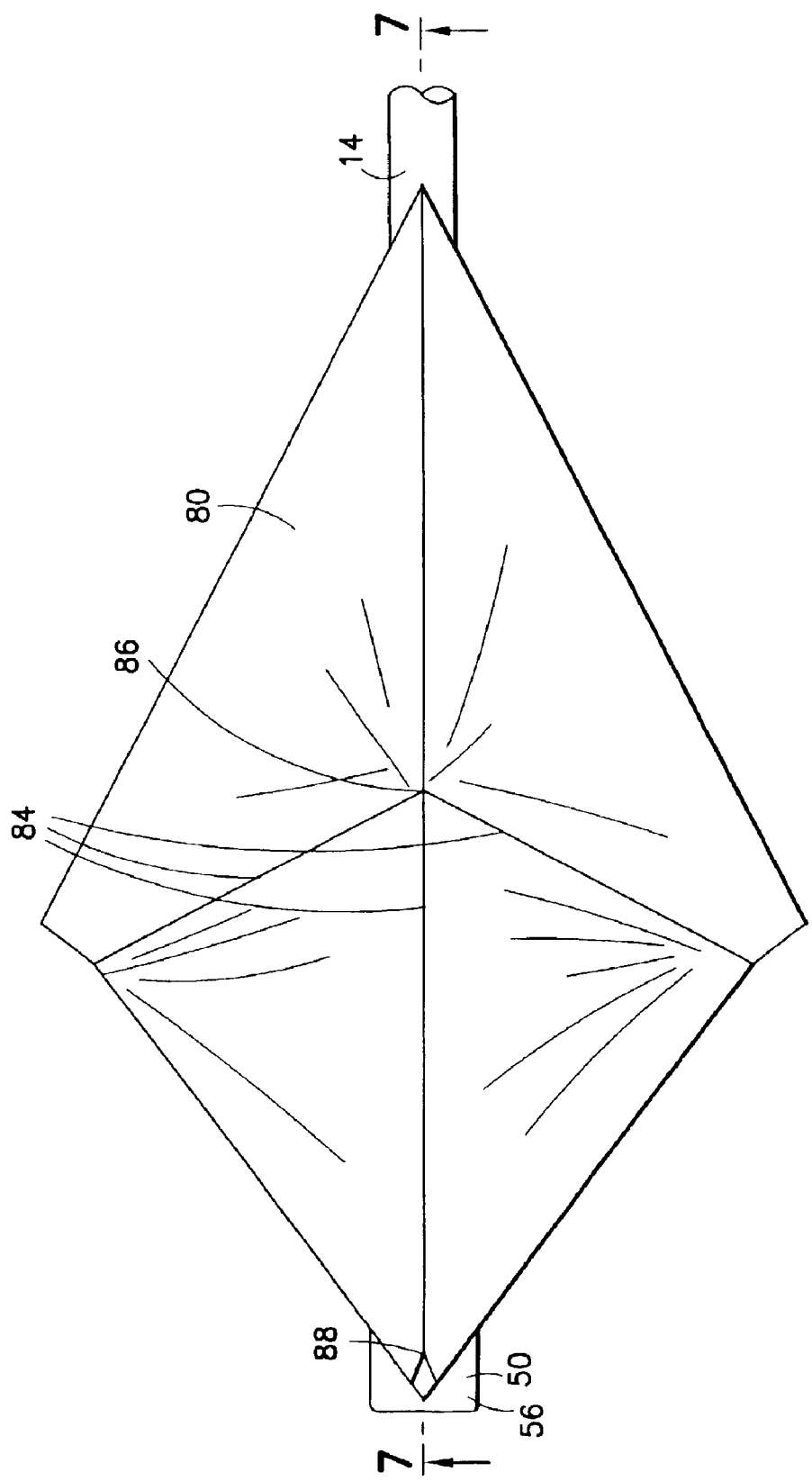
FIG. 6 is a top plan view of the shieldable needle assembly in an extended shielded position.
Figure 7:
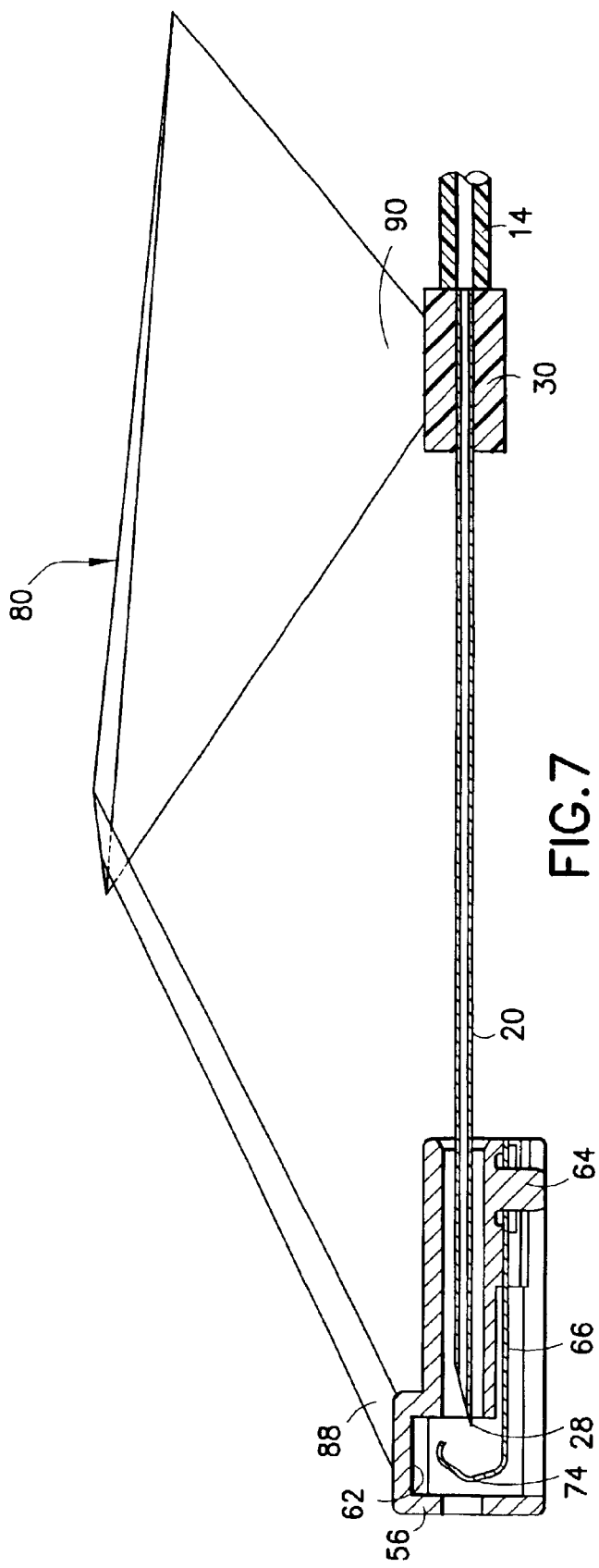
FIG. 7 is a cross-sectional view taken along line 7—7 of FIG. 6.

Referring to the drawings in which like reference characters refer to like parts throughout the several views thereof, FIGS. 1 and 5 illustrate a shieldable needle assembly, for use in connection with a blood collection set, in accordance with the present invention and the related features. The present invention is generally described in terms of a shieldable needle assembly, and encompasses a shieldable needle assembly as well as such a shieldable needle assembly for use with a medical device such as a blood collection set, a hypodermic syringe, a double ended needle assembly for blood collection, and the like. FIGS. 1 and 5 illustrate the shieldable needle assembly in the form of a blood collection set 10, including a shieldable needle device 12. While described in FIGS. 1–5 in terms of one embodiment of a blood collection set, the shieldable needle device of the present invention may incorporate other medical devices used in connection with a needle, such as a hypodermic syringe assembly, a hypodermic needle, a double ended needle assembly for blood collection, an intravenous infusion set, or other fluid handling devices or medical device assemblies that contain piercing elements.

As shown in FIGS. 1 and 5, blood collection set 10 includes a shieldable needle device 12, a flexible tube 14 extending from needle device 12, a fixture 16 mounted to tube 14 and a packaging cover 18 removably mounted to portions of needle device 12 opposite tube 14, such as through a frictional engagement. Shieldable needle device 12 of blood collection set 10 is shown in detail in FIGS. 2–4, and includes a needle cannula 20, a hub 30, a tip guard assembly 50 and a deflectable drive mechanism 80.

Needle cannula 20 includes a proximal end 22 and an opposing distal end 24, with lumen 26 extending through needle cannula 20 from proximal end 22 to distal end 24. Distal end 24 of needle cannula 20 is beveled to define a sharp puncture tip 28, such as an intravenous puncture tip. Puncture tip 28 is provided for insertion into a patient's blood vessel, such as a vein, and is therefore designed to provide ease of insertion and minimal discomfort during venipuncture.

Needle assembly 12 further includes hub 30. Hub 30 is a unitary structure, desirably molded from a thermoplastic material. Hub 30 includes a proximal end 32, a distal end 34, and is defined by a rigid tubular wall 36 extending from proximal end 32 to distal end 34. Tubular wall 36 is characterized by an internal passage 38 extending therethrough from proximal end 32 to distal end 34 of hub 30. Hub 30 further includes a pair of stabilizers 40 extending along tubular wall 36 at opposing sides thereof. Stabilizers 40 provide hub 30, and needle assembly 12, as a butterfly-type wing assembly, assisting in positioning and placement of needle assembly 12 and blood collection set 10 during a blood collection procedure.

Needle cannula 20 is positioned within internal passage 38 of hub 30, and extends from distal end 34 of hub 30. Desirably, needle cannula 20 and hub 30 are separate parts which are fixedly attached and secured through an appropriate medical grade adhesive or the like.

Needle assembly 12 further includes tip guard assembly 50, which is movable along needle cannula 20 between a first proximal position adjacent hub 30, and a second distal position adjacent puncture tip 28, as will be described in more detail herein. Tip guard assembly 50 includes a housing 52 and a protective clip 60. Housing 52 is a unitary structure, desirably molded from a thermoplastic material, including a proximal end 54, a distal end 56, and an internal passage 58 extending between the ends. Portions of internal passage 58 adjacent distal end 56 define an enlarged clip receptacle 62, as shown in FIG. 4. A clip mounting post 64 extends downwardly from housing 52 at a location near proximal end 54 of housing 52.

Clip 60 is unitarily stamped and formed from a resiliently deflectable metallic material. Clip 60 includes a planar spring leg 66 with a proximal end 68 and an opposed distal end 70. A mounting aperture 72 extends through spring leg 66 at a location near proximal end 68. Mounting aperture 72 has a diameter approximately equal to or slightly less than the diameter of mounting post 64 of housing 52. As such, mounting post 64 can be forced through mounting aperture 72 when the axis of mounting post 64 and the axis of mounting aperture 72 are substantially collinear. A lock out leg 74 extends angularly from distal end 70 of spring leg 66. Lock out leg 74 is bent back toward proximal end 68 of clip 60. The bends in lock out leg 74 enable secure protective engagement with puncture tip 28 of needle cannula 20 and further enable smooth axial sliding movement of tip guard assembly 50 along needle cannula 20 as described in further detail herein.

Figure 8:
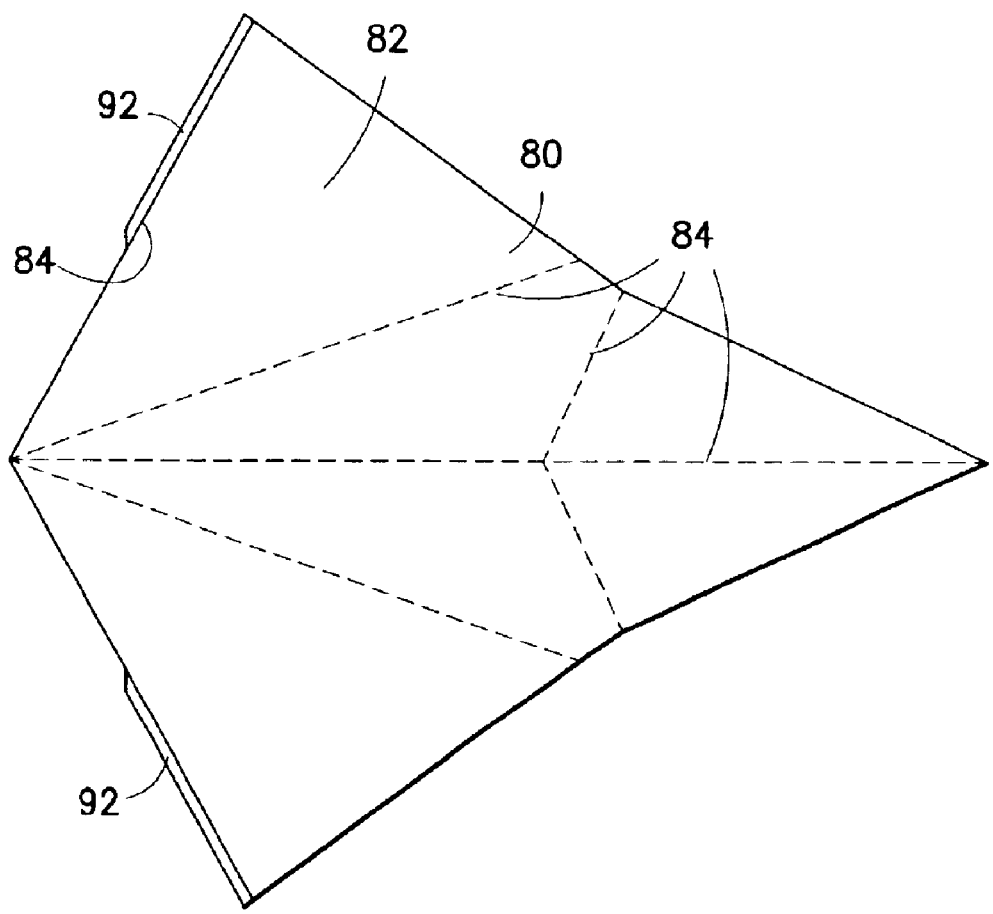
FIG. 8 is a top plan view of a planar sheet material depicting a fold pattern for forming one embodiment of a drive mechanism for use in the blood collection set of the present invention.

Hub 30 and tip guard assembly 50 are interconnected through drive mechanism 80. Drive mechanism 80 provides for axial movement of tip guard assembly 50 along needle cannula 20 from a first proximal position adjacent hub 20 to a second distal position adjacent puncture tip 28, as will be described in more detail herein. Drive mechanism 80 is a unitary structure of a planar sheet material 82, as shown in FIG. 8. Planar sheet 82 includes a plurality of folds 84 in a patterned arrangement to form drive mechanism 80 in a first shape, which is adapted to maintain tip guard assembly 50 in the first proximal position adjacent hub 20. Moreover, folds 84 of planar sheet 82 further provide drive mechanism 80 with the ability to deflect from such a first shape to a second extended shape, in which tip guard assembly 50 is moved to a second distal position adjacent puncture tip 28.

Planar sheet 82 of drive mechanism 80 is desirably constructed of a material which is a rigid flexible material. More particularly, a rigid flexible material is defined in terms of the present invention as a material which is sufficiently rigid to maintain a desired self-supporting shape when folded, for example along folds 84, yet is sufficiently flexible to deflect from such a desired self-supporting shape with at least some of the folds unfolding, to provide a second shape different from the first shape. Examples of materials which are rigid yet flexible in this manner include paper and plastic, for example, polypropylene, formed into a planar sheet.

Planar sheet 82 can be folded along folds 84 as shown in FIG. 8, to form a shape as shown in FIGS. 1–5. Such a folded structure is shaped in the form of a dorsal fin extending along the top of needle device 12 of blood collection set 10. Such a shape provides drive mechanism 80 with a first portion 88 which is adapted for attachment to tip guard assembly 50, and a second portion 90 which is adapted for attachment to hub 30. First portion 88 is desirably a folded portion of planar sheet 82 which is fixedly adhered to a top portion of housing 52 of tip guard assembly 50, such as through an adhesive or the like. Similarly, second portion 90 may be a folded portion of planar sheet 82, such as flaps 92 depicted in FIG. 8, which are fixedly adhered to tubular wall 36 of hub 30, desirably at the top portion of tubular wall 36. As such, drive mechanism 80 interconnects hub 30 and tip guard assembly 50. Further, the folded structure of drive mechanism 80 provides a first, self-supporting shape, which maintains tip guard assembly 50 in a first proximal position adjacent hub 20.

Moreover, the rigid flexible material of planar sheet 82 allows for planar sheet 82 to deflect from this first shape into a second shape. For example, folds 84 of planar sheet 82, which define the shape of the folded structure of drive mechanism 80 in the form of a dorsal fin, also provide drive mechanism 80 with a juncture of a plurality of folds 84, such as trigger 86 at the top portion thereof. External pressure exerted on trigger 86 in a direction of arrow 100, such as through a user's index finger, activates drive mechanism 80 and causes at least some of folds 84 of drive mechanism 80 to partially or fully unfold, thereby acting as a hinge. Unfolding of folds 84 in this manner results in a biasing force exerted between first portion 88 and second portion 90 of drive mechanism 80 in opposing directions with respect to each other. Since second portion 90 of drive mechanism 80 is fixedly attached to hub 30 and hub 30 is stationary with respect to needle device 12 and flexible tube 14, second portion 90 of drive mechanism 80 remains in a fixed location. Since first portion 88 of drive mechanism 80 is fixedly attached to tip guard assembly 50 and since tip guard assembly 50 is axially movable along needle cannula 20, such biasing force of first portion 88 and second portion 90 in opposing directions causes tip guard assembly to axially move in the direction of arrow 102 away from hub 30 and toward distal end 24 of needle cannula 20, where tip guard assembly 50 can effectively shield puncture tip 28.

Tip guard assembly 50 moves axially along needle cannula 20 toward distal end 24 during the deflection of drive mechanism 80 between the first shape and the second shape. Such deflection of drive mechanism 80 is provided for through the plurality of folds 84, which form at least one, and more desirably a plurality of living hinges for drive mechanism 80. These living hinges are capable of maintaining drive mechanism 80 in the first shape which is self-supporting, and are capable of unfolding into the second shape. The unique shape and configuration of drive mechanism 80 also results in drive mechanism 80 being capable of unfolding into a low profile flat shape, in addition to providing for axial movement of tip guard assembly 50 upon activation of trigger 86 through exertion of force in a direction of arrow 100.

Planar sheet 82 of drive mechanism 80 may further include a material which is capable of adding flexible memory to drive mechanism 80. In particular, a metallic or plastic portion may be associated with planar sheet 82, to provide planar sheet 82 with potential energy to allow for planar sheet 82 to deflect from the first shape into the second shape. Such a material may desirably be integral with the entire surface of planar sheet 82, or may be integral with a portion of planar sheet 82, such as a portion of planar sheet 82 at one or more folds 84. For example, a metallic or plastic portion may be laminated to a portion of planar sheet 82, with the metallic or plastic portion providing the rigid flexibility to planar sheet 82.

Assembly of blood collection set 10 is accomplished by folding planar sheet 82 along folds 84 and forming into the shape of a dorsal fin to provide drive mechanism 80. First portion 88 of drive mechanism 80 is fixedly adhered to tip guard housing 52, and second portion 90 of drive mechanism 80 is fixedly adhered to hub 20. Tip guard assembly 50 is assembled by forcing mounting post 64 of tip guard housing 52 through mounting aperture 72 of clip 60. Spring leg 66 of clip 60 is then urged downwardly or away from internal passage 58 through tip guard housing 52. Distal end 22 of needle cannula 20 is then passed through internal passage 38 of hub 30, and urged into internal passage 58 at proximal end 54 of tip guard housing 52. The downward deflection of spring leg 66 enables distal end 24 of needle cannula 20 to be passed entirely through tip guard housing 52. Spring leg 66 can be released after puncture tip 28 of needle cannula 20 passes entirely through tip guard housing 20. Thus, the end of lock out leg 74 will be biased against and slide along needle cannula 20. Tip guard assembly 50 then is slid proximally along needle cannula 20 into a position adjacent hub 22. Packaging cover 18 is then urged over puncture tip 28 and urged proximally over needle cannula 20, with puncture tip 28 safely maintained and disposed within packaging cover 18.

Blood collection set 10 can be packaged substantially in the condition shown in FIG. 5, with drive mechanism 80 in a folded state. Prior to use, blood collection set 10 is removed from its package. Fixture 16 then may be connected to an appropriate receptacle for providing fluid communication with lumen 26 through needle cannula 20.

In use, blood collection set 10 is provided with needle device 12 assembled and including flexible tube 14 extending from needle device 12 and connected to fixture 16. After removing blood collection set 10 from its package, it can be assembled with other appropriate medical equipment for use. For example, a non-patient needle assembly and a needle holder may be connected to blood collection set 10 through fixture 16.

To prepare for use of blood collection set 10, the user grasps blood collection set 10 at needle device 12, holding drive mechanism 80 in a folded state to ensure that tip guard assembly 50 is maintained adjacent hub 30. Packaging cover 18 is then grasped and urged distally to disengage from needle cannula 20, thereby exposing puncture tip 28 of needle cannula 20.

The medical practitioner can then urge puncture tip 28 at distal end 24 of needle cannula 20 into a targeted blood vessel of a patient, while drive mechanism 80 is maintained in a folded state, between thumb and forefinger to assist in controlled entry by the medical practitioner. Stabilizers 40 are maintained flush against the patient's skin during such procedure, thereby ensuring that needle device 12 is inserted in the proper orientation within the vessel. After the targeted blood vessel has been accessed, the medical practitioner can release the grip on drive mechanism 80. Drive mechanism 80 maintains its shape, with tip guard assembly 50 held adjacent hub 30.

An appropriate medical procedure can then be conducted. Upon completion of the procedure, such as when all desired samples have been drawn, needle cannula 20 is withdrawn from the patient, and activation of the safety feature of needle device 12 can be accomplished.

To activate the safety feature, trigger 86 of drive mechanism 80 is activated by exerting pressure in a direction of arrow 100, such as by pushing on the point at the common juncture of folds 84 at the top of drive mechanism 80. Such force unfolds some or all of folds 84, thereby deflecting drive mechanism 80 from a first folded shape to a second unfolded shape. During such unfolding of drive mechanism 80, tip guard assembly 50 is forced in an axial direction of arrow 102 and slides or glides along needle cannula 20 toward distal end 24.

After tip guard assembly 50 is moved along needle cannula 20 to the distal end 24, lockout leg 74 of clip 60 will pass distally beyond puncture tip 28 of needle cannula 20. The inherent resiliency of spring leg 66 of clip 60 will urge lockout leg 74 over puncture tip 28 of needle cannula 20. Thus, a return movement of tip guard assembly 50 is prevented. Furthermore, planar sheet 82 of drive mechanism 80 has an overall dimension that will prevent movement of tip guard assembly 50 distally beyond needle cannula 20. Hence, puncture tip 28 of needle cannula 20 is safely shielded. Furthermore, inadvertent contact with portions of needle cannula 20 between the opposed ends is substantially prevented by the overall dimensions of drive mechanism 80 in an unfolded state at least partially encompassing needle cannula 20. Blood collection set 10 may then be appropriately discarded.

It is noted that activation of the safety feature may be accomplished while venipuncture is maintained, that is while puncture tip 28 of needle cannula 20 is maintained within the blood vessel of the patient. For example, trigger 86 can be activated while puncture tip 28 is within the patient's blood vessel, thereby axially moving tip guard assembly 50 axially along needle cannula 20. Since puncture tip 28 is within the patient's blood vessel, such distal movement of tip guard assembly 50 will terminate when tip guard housing 52 contacts the skin of the patient near the puncture site. Upon removal of puncture tip 28 from the patient's blood vessel, tip guard assembly 50 will continue in it's axial movement toward the distal end 24 of needle cannula 20 due to the bias exerted through folds 84 of drive mechanism 80. Such axial movement results in lockout leg 74 being urged over puncture tip 28 of needle cannula 20, thereby shielding puncture tip 28 of needle cannula 20.

FIGS. 9–14 depict further embodiments of the invention that includes many components which are substantially identical to the components of FIGS. 1–8. Accordingly, similar components performing similar functions will be numbered identically to those components of FIGS. 1–8, except that a suffix "a" will be used to identify those similar components in FIGS. 9–11, a suffix "b" will be used to identify those similar components in FIG. 12, and a suffix "c" will be used to identify those similar components in FIGS. 13–14.

Figure 9:
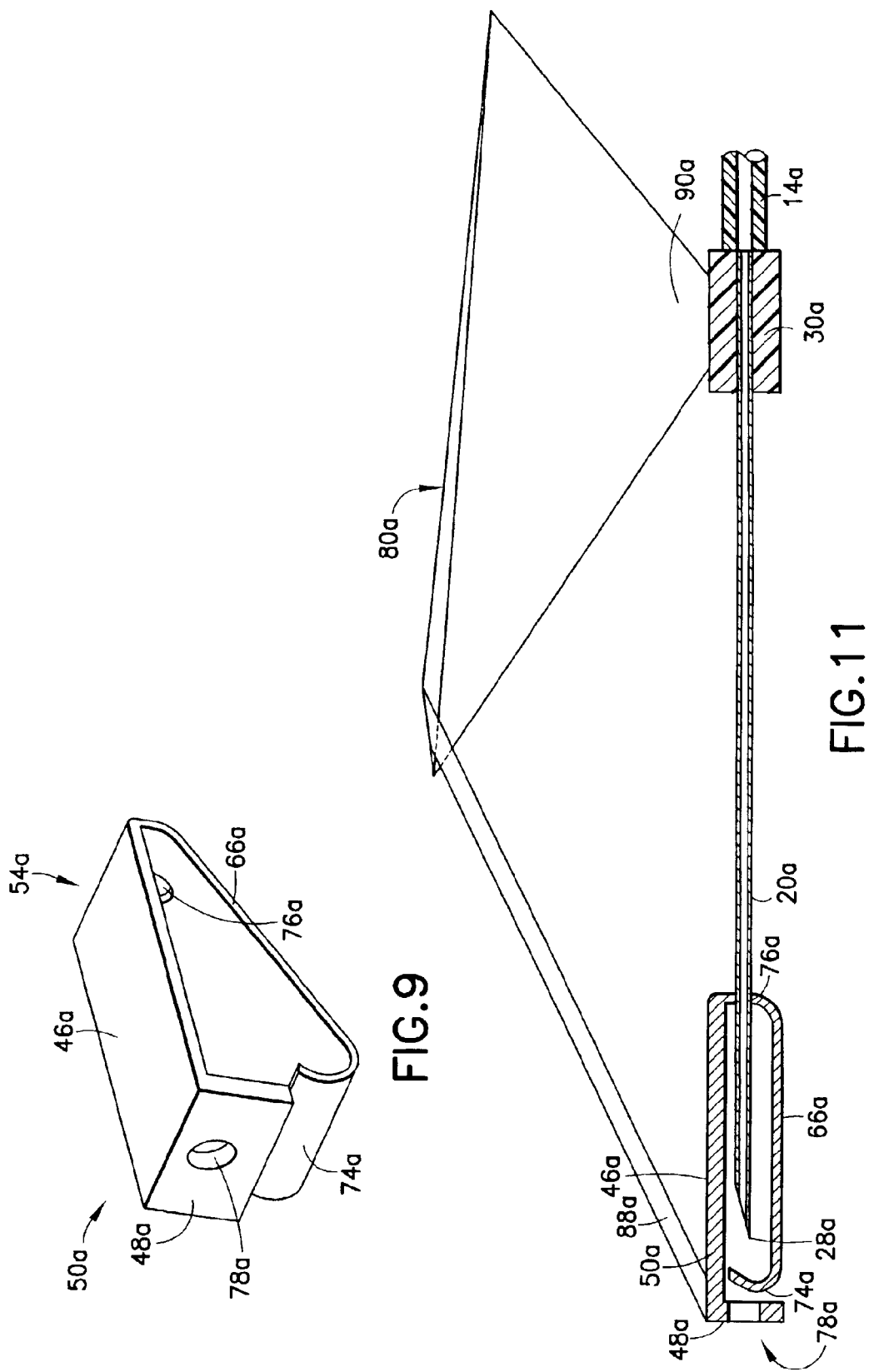
FIG. 9 is a perspective view of an alternate tip guard assembly for use in connection with the present invention.
Figure 10:
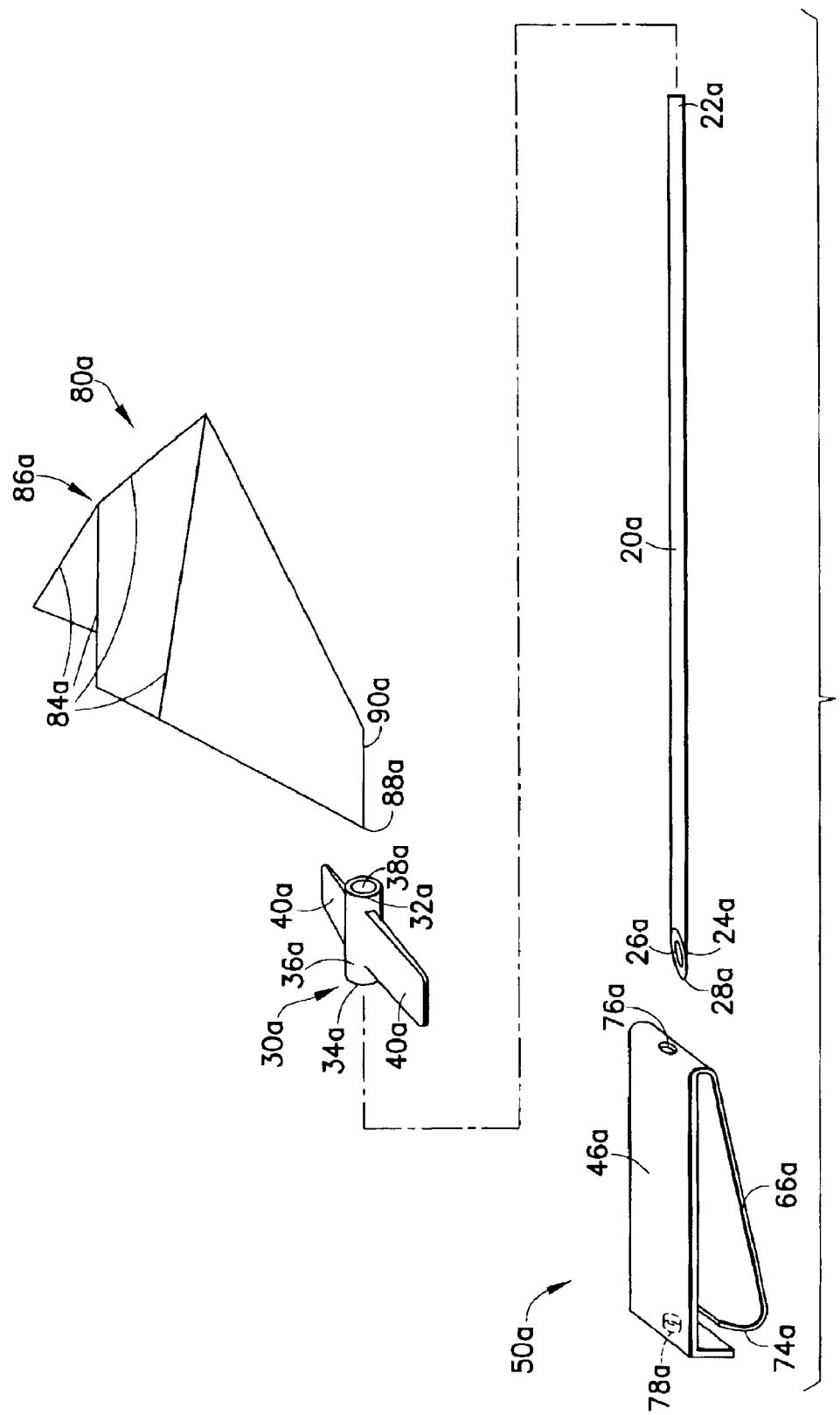
FIG. 10 is an exploded perspective view of the shieldable needle assembly including the alternate tip guard assembly of FIG. 9.

In an alternate embodiment of the present invention, tip guard assembly 50a may be provided as a one component tip guard assembly, as depicted in FIGS. 9–11. More particularly, as shown in FIG. 9, alternate tip guard assembly 50a is movable along needle cannula 20a between a first proximal position adjacent hub 30a, and a second distal position adjacent puncture tip 28a, in a similar manner as with tip guard assembly 50 described above in connection with the embodiments of FIGS. 1–8. Tip guard assembly 50a includes proximal end 54a and distal end 56a, with top extent 46a defining the top portion of tip guard assembly 50a and extending longitudinally along a portion of needle cannula 20a between proximal end 54a and distal end 56a. Top extent 46a bends downwardly at distal end 56a to form front end wall 48a. At proximal end 54a, top extent 46a bends backward to form spring leg 66a which extends back toward the distal end 56a of tip guard assembly 50a, with lock out leg 74a bending upward and backward to form an end wall, as seen in FIGS. 9–11. Proximal end 54a of tip guard assembly 50a includes proximal opening 76a, while distal end 56a of tip guard assembly 50a includes distal opening 78a extending through front end wall 48a. Proximal opening 76a and distal opening 78a are provided for accommodating needle cannula 20a extending therethrough.

As with the embodiment described in connection with FIGS. 1–8, tip guard assembly 50a is interconnected with hub 30a through drive mechanism 80a, with first portion 88a of drive mechanism 80a attached to top extent 46a of tip guard assembly 50a. Tip guard assembly 50a is movable between a proximal position substantially adjacent hub 30a, and a distal position, in which tip guard assembly 50a protectively surrounds puncture tip 28a of needle cannula 20a, as described above. In the proximal position, needle cannula 20a extends through proximal opening 76a and distal opening 78a, with spring leg 66a biased against needle cannula 20a. During unfolding of drive mechanism 80a as discussed above, tip guard assembly 50a slides or glides along needle cannula 20a toward distal end 24a, in a similar manner as discussed above. As shown in FIG. 11, distal opening 78a and lock out leg 74a pass distally beyond puncture tip 28a, and the inherent resiliency of spring leg 66a urges lock out leg 74a over puncture tip 28, preventing a return movement, and thus preventing re-exposure of puncture tip 28.

While the needle assembly of the present invention has been described in terms of an embodiment for use in connection with a blood collection system, it is further contemplated that the needle assembly could be used with other medical procedures, such as in conjunction with a conventional intravenous infusion set, a hypodermic needle assembly, or a double ended needle assembly for blood collection, all of which are well known in the art for use with needle assemblies.

For example, FIG. 12 depicts safety needle device 12b for attachment to conventional medical devices, such as conventional needle holders for blood collection, syringes, and the like. As shown in FIG. 12, the safety needle device 12b includes a needle cannula 20b, a hub 30b, and a tip guard assembly 80b, as set forth in the embodiment described above. In the embodiment of FIG. 12, the safety needle device 12b is an independent component for attachment to a medical device. As such, hub 30b acts as a base hub for providing such attachment.

Accordingly, hub 30b includes means for attachment with a medical device, such as a hypodermic syringe, at proximal end 32b. For example, hub 30b may include a threaded end at the proximal end thereof. Desirably, as shown in FIG. 12, hub 30b includes a female luer fitting 104 and a luer flange 106 at the proximal end thereof. Such an arrangement provides for attachment with a luer fitting, and may include additional luer lugs for attachment with a luer collar, such as a syringe luer collar. Such a luer fitting enables safety needle device 12b to be sold as a sterile needle assembly for use with a conventional medical device adapted for use with a luer fitting, such as a hypodermic syringe.

Figure 13:
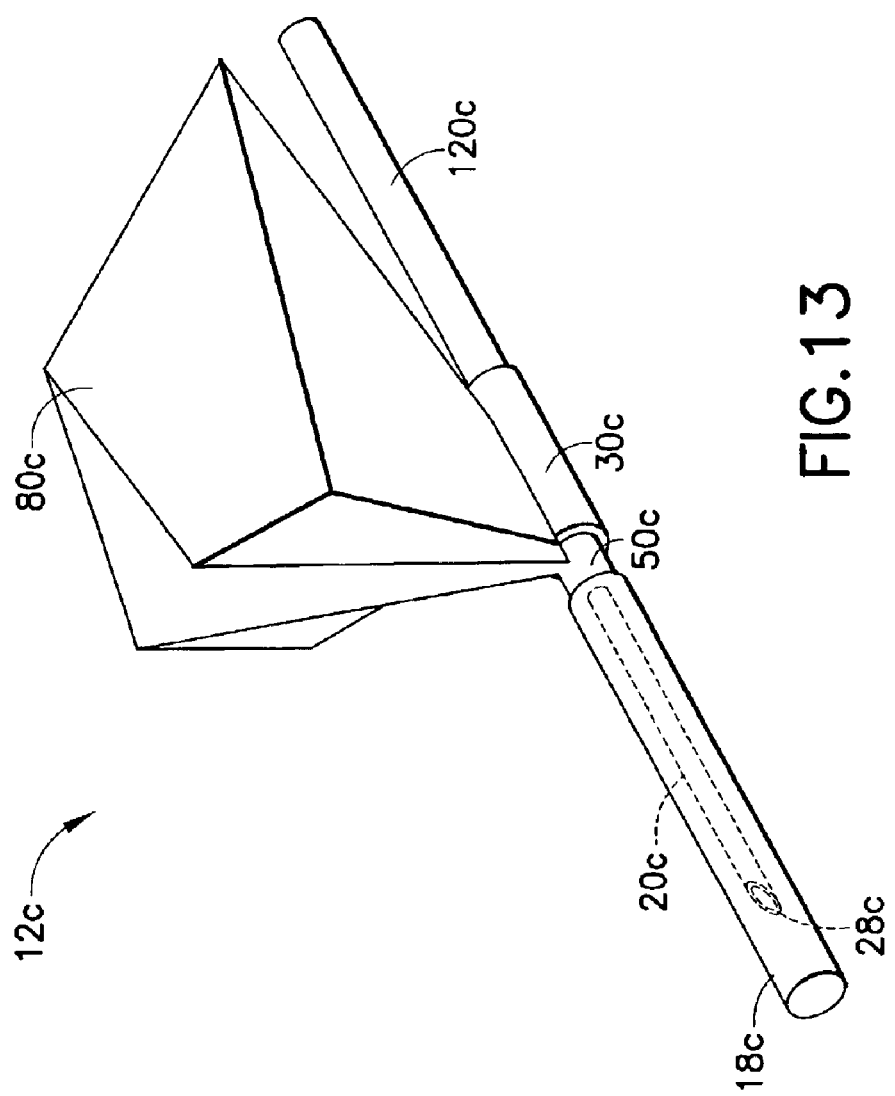
FIG. 13 is a perspective view of a double ended needle assembly for attachment to a needle holder in accordance with a further embodiment of the present invention.
Figure 14:
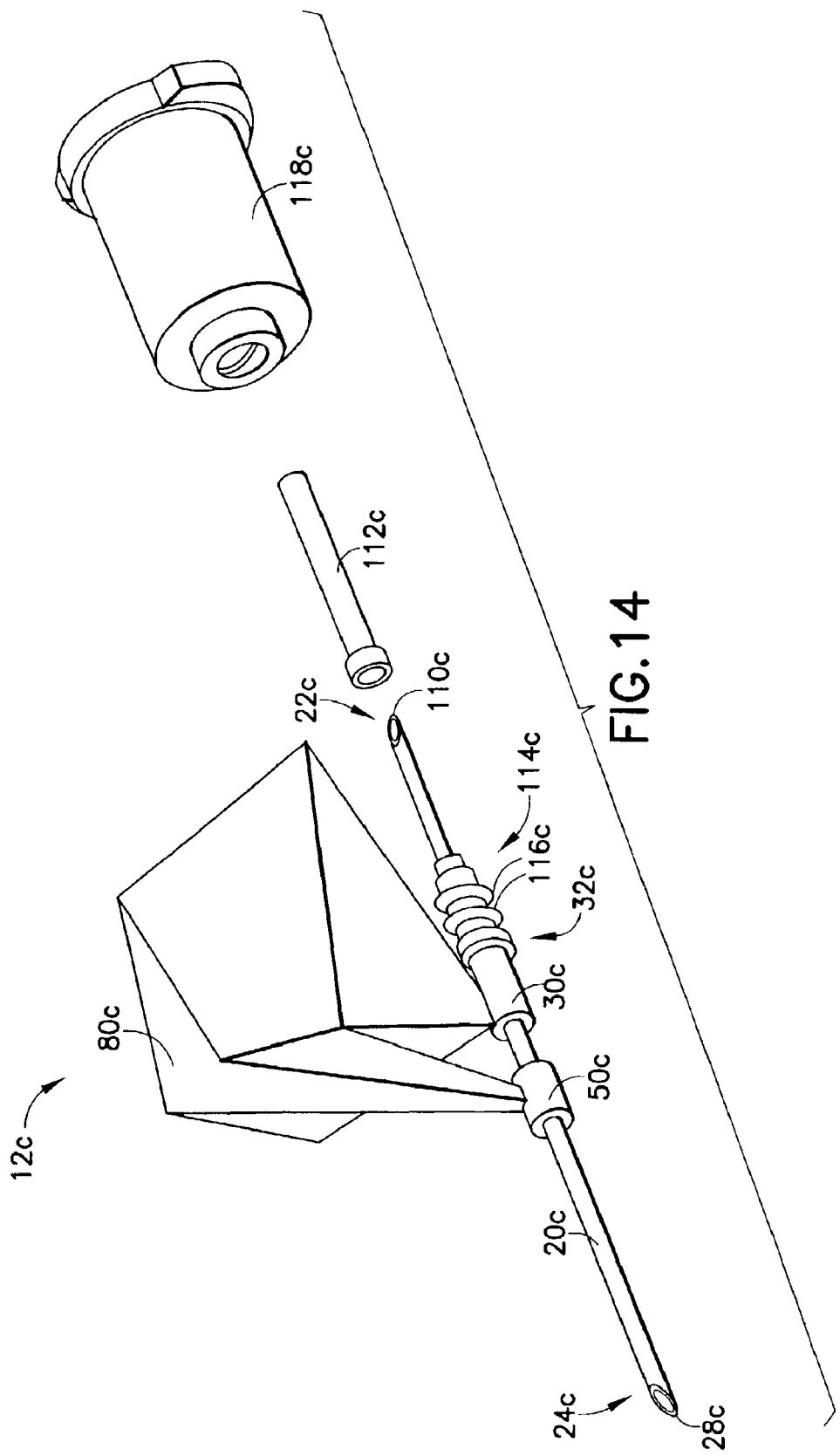
FIG. 14 is an exploded perspective view of the double ended needle assembly of FIG. 13 with the needle covers removed and shown with a needle holder.

In a further embodiment depicted in FIGS. 13 and 14, safety needle device 12c is provided as an independent component in the form of a double ended needle assembly for attachment to a needle holder, as is known for use in connection with blood sampling procedures. In the needle device 12c depicted in FIGS. 13 and 14, needle cannula 20c is in the form of a double ended needle, including puncture tip 28c as an intravenous puncture tip at distal end 24c thereof, and a non-patient puncture tip 10c at proximal end 22c thereof. Needle cannula 20c extends through hub 30c. Proximal end 22c of needle cannula 20c desirably includes an elastomeric sleeve 112c covering non-patient puncture tip 110c.

Hub 30c desirably includes means for attachment to a needle holder 118. For example, hub 30c may include a threaded end 114c at the proximal end 32c thereof. Preferably, threaded end 114c comprises male threads 116c for mounting needle device 12c on needle holder 118c. As needle device 12c is provided as an independent component for attachment to a separate needle holder, needle device 12c is desirably packaged as shown in FIG. 13, including packaging cover 18c covering distal end 24c of needle cannula 20c, and further including a second packaging cover 120c covering proximal end 22c of needle cannula 20c.

While the present invention is satisfied by embodiments in many different forms, there is shown in the drawings and described herein in detail, the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

What is claimed:

1. A shieldable needle device comprising:
   a needle cannula having opposed proximal and distal ends;
   a tip guard axially movable along said needle cannula from a proximal position substantially adjacent said proximal end of said needle cannula to a distal position where said tip guard protectively surrounds said distal end of said needle cannula; and
   a drive mechanism connected to said tip guard for moving said tip guard from said proximal position to said distal position, said drive mechanism comprising a unitary structure including a plurality of folds with at least two of said folds defining intersecting hinges at a common juncture to form a trigger, said drive mechanism capable of maintaining a first self-supporting shape for maintaining said tip guard in said proximal position and which is deflectable from said first self-supporting shape to a second extended shape in which said tip guard is moved to said distal position when a force is applied to said trigger, thereby causing said intersecting hinges defined by the folds to at least partially unfold from said common juncture.

2. A needle device as in claim 1, wherein said unitary structure comprises a rigid flexible planar sheet material including a plurality of folds.

3. A needle device as in claim 1, further comprising a hub mounted to said proximal end of said needle cannula, said drive mechanism interconnecting said hub and said tip guard.

4. A needle device as in claim 1, wherein said drive mechanism is in the form of a dorsal fin extending along said needle device.

5. A shieldable needle device comprising:
   a) a needle cannula having opposed proximal and distal ends;
   b) a hub mounted to said proximal end of said needle cannula;
   c) a tip guard axially movable along said needle cannula from a proximal position substantially adjacent said hub to a distal position where said tip guard protectively surrounds said distal end of said needle cannula; and
   d) a drive mechanism for moving said tip guard from said proximal position to said distal position, said drive mechanism comprising a unitary planar material interconnected between said hub and said tip guard, said planar material including a plurality of folds with at least two of said folds defining intersecting hinges to form a dorsal fin extending along said needle device for providing said drive mechanism with at least one trigger, said at least one trigger and said intersecting hinges interrelating for movement of said tip guard from said proximal position to said distal position upon activation of said at least one trigger to cause said folds to at least partially unfold.

6. A needle device as in claim 5, wherein said planar material comprises a rigid flexible material.

7. A needle device as in claim 6, wherein said planar material comprises a plastic material.

8. A needle device as in claim 7, wherein said plastic material is polypropylene.

9. A needle device as in claim 6, wherein said planar material comprises paper.

10. A needle device as in claim 5, wherein at least two of said intersecting hinges intersect at a common juncture to form said trigger.

11. A needle device as in claim 5, wherein external pressure exerted on said trigger causes at least one of said plurality of folds to unfold, thereby activating said drive mechanism and causing said tip guard to move to said distal position.

12. A needle device as in claim 5, wherein said tip guard comprises a tip guard housing formed from a plastic material, a metallic spring clip being mounted to said housing, said spring clip being biased against said needle cannula when said tip guard is in said proximal position and being resiliently moved over said distal end of said needle cannula when said tip guard is in said distal position.

13. A needle device as in claim 5, wherein said hub is adapted for connection to a flexible tube of a blood collection set.

14. A needle device as in claim 5, wherein said hub further includes means for attachment with a hypodermic syringe.

15. A shieldable blood collection set comprising:
   a fixture for connecting said blood collection set to a receptacle;
   a flexible tube having opposed first and second ends, said first end of said flexible tube being connected to said fixture;
   a hub mounted to said second end of said flexible tube;
   a needle cannula having a proximal end connected to said hub, a distal end projecting from said hub and a lumen in fluid communication with said flexible tube and said fixture;
   a tip guard axially movable along said needle cannula from a proximal position substantially adjacent said hub to a distal position surrounding said distal end of said needle cannula; and
   a drive mechanism for moving said tip guard from said proximal position to said distal position, said drive mechanism comprising a planar material securely interconnected between said hub and said tip guard, said planar material including a plurality of folds with at least two of said folds defining intersecting hinges at a common juncture to form at least one trigger for activation of said drive mechanism for moving said tip guard from said proximal position to said distal position, wherein external pressure exerted on said trigger causes at least one of said plurality of folds to unfold at said intersecting hinges, thereby activating said drive mechanism and causing said tip guard to move to said distal position.

16. A blood collection set as in claim 15, further comprising a packaging cover frictionally engaged on said needle cannula and securely surrounding said needle cannula.

17. A blood collection set as in claim 15, wherein said tip guard comprises a rigid housing having an aperture extending therethrough, said needle cannula being slidably disposed in said aperture, said tip guard further comprising a metallic clip mounted to said housing and configured for sliding engagement against said needle cannula as said tip guard moves from said proximal position toward said distal position, said metallic clip being dimensioned and disposed to protectively cover said distal end of said needle cannula when said tip guard has reached said distal position.

18. A blood collection set as in claim 15, wherein said planar material comprises a rigid flexible material.

19. A blood collection set as in claim 15, wherein said planar material comprises paper.

20. A blood collection set as in claim 15, wherein said planar material comprises a plastic material.

21. A blood collection set as in claim 15, wherein said drive mechanism is in the form of a dorsal fin extending along said needle device.

22. A shieldable double ended needle assembly comprising:
   a hub including a proximal end and a distal end and an internal passage extending therethrough;
   a needle cannula extending through the internal passage of said hub, said needle cannula including a distal end with an intravenous puncture tip projecting from said distal end of said hub and a proximal end with a non-patient puncture tip projecting from said proximal end of said hub;
   a tip guard axially movable along said needle cannula from a proximal position substantially adjacent said hub to a distal position surrounding said intravenous puncture tip at said distal end of said needle cannula; and
   a drive mechanism for moving said tip guard from said proximal position to said distal position, said drive mechanism comprising a planar material securely interconnected between said hub and said tip guard, said planar material including a plurality of folds with at least two of said folds defining intersecting hinges at a common juncture to form at least one trigger for activation of said drive mechanism for moving said tip guard from said proximal position to said distal position, wherein external pressure exerted on said trigger causes at least one of said plurality of folds to unfold at said intersecting hinges, thereby activating said drive mechanism and causing said tip guard to move to said distal position.

23. A needle assembly as in claim 22, wherein said proximal end of said hub includes means for attachment with a needle holder.

24. A needle assembly as in claim 23, wherein said means comprises threads.

25. A needle assembly as in claim 22, further comprising a packaging cover extending over the distal end of the needle cannula.

26. A needle assembly as in claim 25, further comprising a second packaging cover extending over the proximal end of the needle cannula.

\* \* \* \* \*